United States Patent [19]

Bryan et al.

[11] Patent Number: 5,582,165
[45] Date of Patent: Dec. 10, 1996

[54] PRE-ASSEMBLED SEALED, SHEATHED CATHETERS AND RELATED VALVE ELEMENTS WITH QUICK DISCONNECT MEANS FOR ENDOTRACHEAL SUCTIONING

[76] Inventors: James F. Bryan, 52 Yacht Club Dr. Apt. 403, North Palm Beach, Fla. 33408; Blaine E. Beck, 1895 LeDieu Rd., Roswell, Ga. 30075

[21] Appl. No.: 852,181

[22] PCT Filed: Aug. 22, 1991

[86] PCT No.: PCT/US91/05827

§ 371 Date: Jun. 30, 1994

§ 102(e) Date: Jun. 30, 1994

[87] PCT Pub. No.: WO93/03777

PCT Pub. Date: Mar. 4, 1993

Related U.S. Application Data

[63] Continuation-in-part of Ser. No. 520,787, May 8, 1990, abandoned, which is a continuation-in-part of Ser. No. 158,587, Feb. 28, 1988, abandoned.

[51] Int. Cl.[6] .................... A61M 1/00; A61M 39/00
[52] U.S. Cl. .................. 128/207.14; 128/207.15; 128/207.16; 128/909; 128/912; 604/163
[58] Field of Search ............ 128/202.27, 909, 128/912, 207.15, 207.16, 200.26, 205.12, 207.14, 205.19, 911; 604/163, 192, 263, 267, 171

[56] References Cited

U.S. PATENT DOCUMENTS

| | | | |
|---|---|---|---|
| 3,035,691 | 5/1962 | Rasmussen et al. | 604/171 |
| 3,347,566 | 10/1967 | Nelson . | |
| 4,170,996 | 10/1979 | Wu | 604/171 |
| 4,193,406 | 3/1980 | Jinotti | 128/205.19 |
| 4,850,350 | 7/1989 | Jackson | 128/207.16 |
| 4,967,743 | 11/1990 | Lambert | 128/207.16 |
| 5,088,486 | 2/1992 | Jinotti | 128/200.26 |
| 5,125,522 | 6/1993 | Page et al. | 604/163 |
| 5,191,881 | 3/1993 | Beck | 128/207.16 |
| 5,255,676 | 10/1993 | Russo | 128/207.16 |

*Primary Examiner*—Edgar S. Burr
*Assistant Examiner*—V. Srivastava

[57] ABSTRACT

A package for a catheter which may be connected to a fluid source, the source and catheter having quick disconnect means, the package comprising an elongated envelope of flexible plastic sheet material such as polyethylene. The package converts to a protective sheath when the catheter and its envelope are connected to the fluid source, such connection anchoring the sheath to such source while forming a fluid seal between the quick disconnect means. The sheath/envelope reconverts to a package for disposal of the catheter after use.

1 Claim, 6 Drawing Sheets

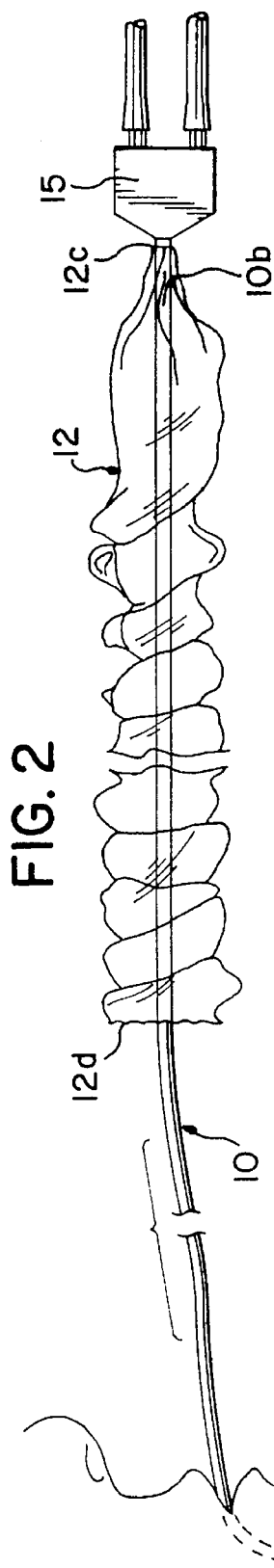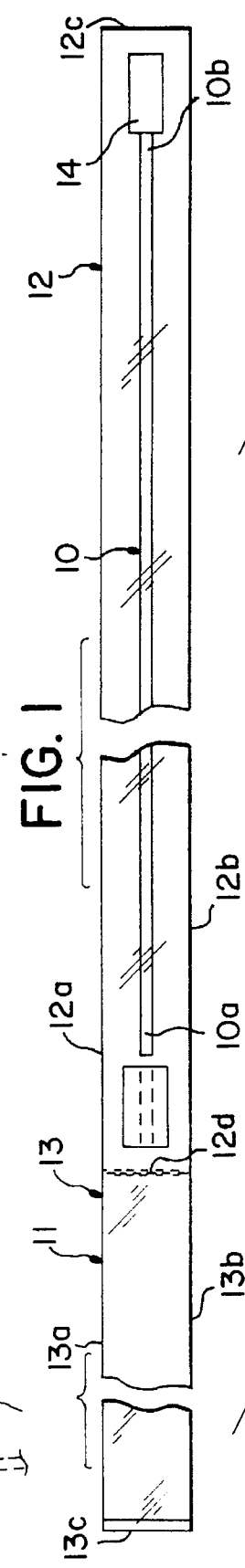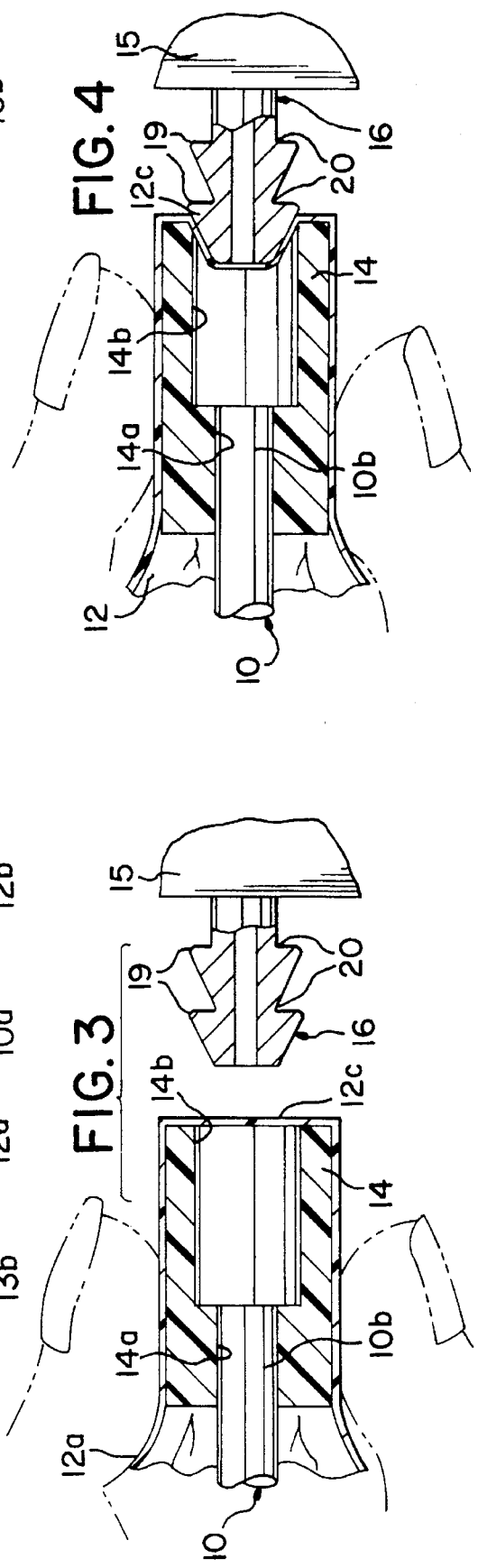

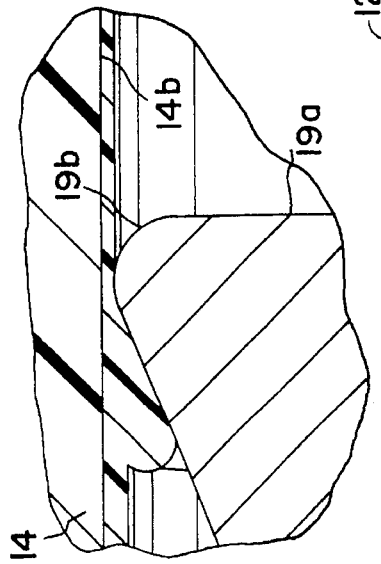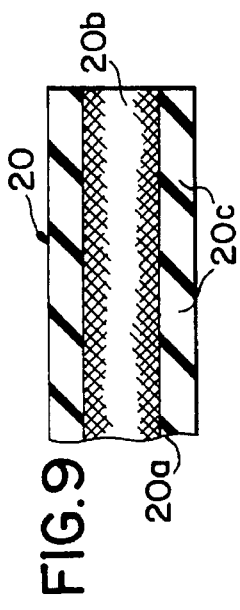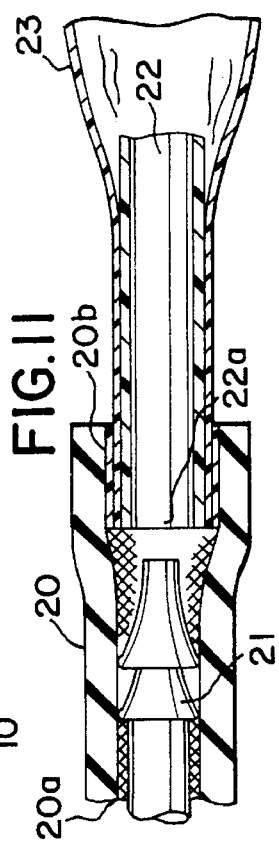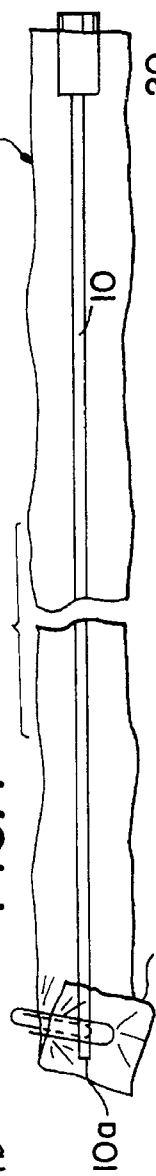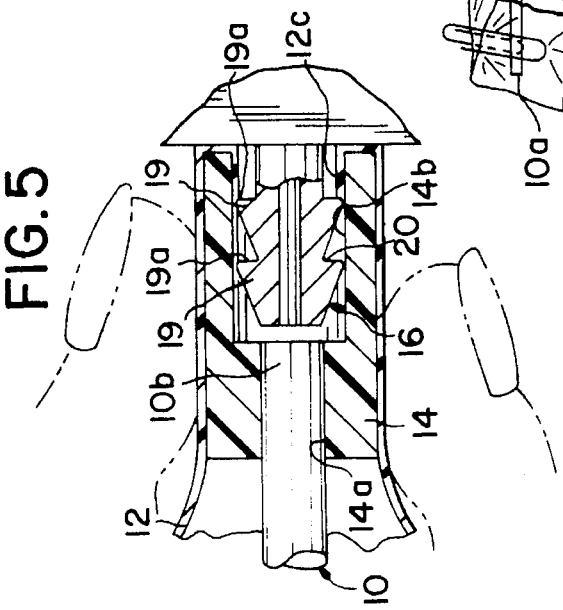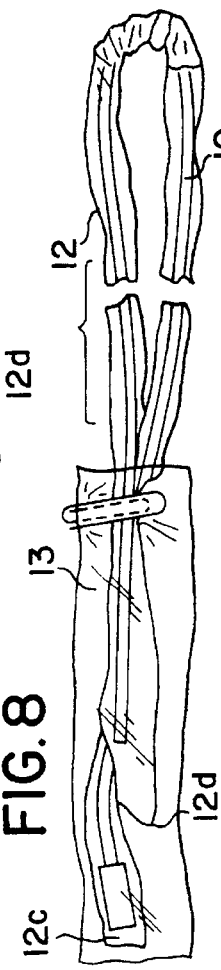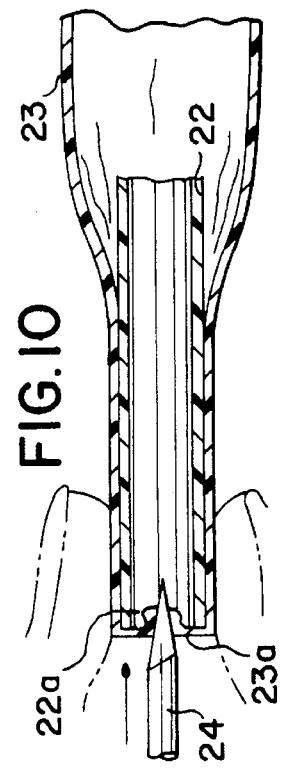

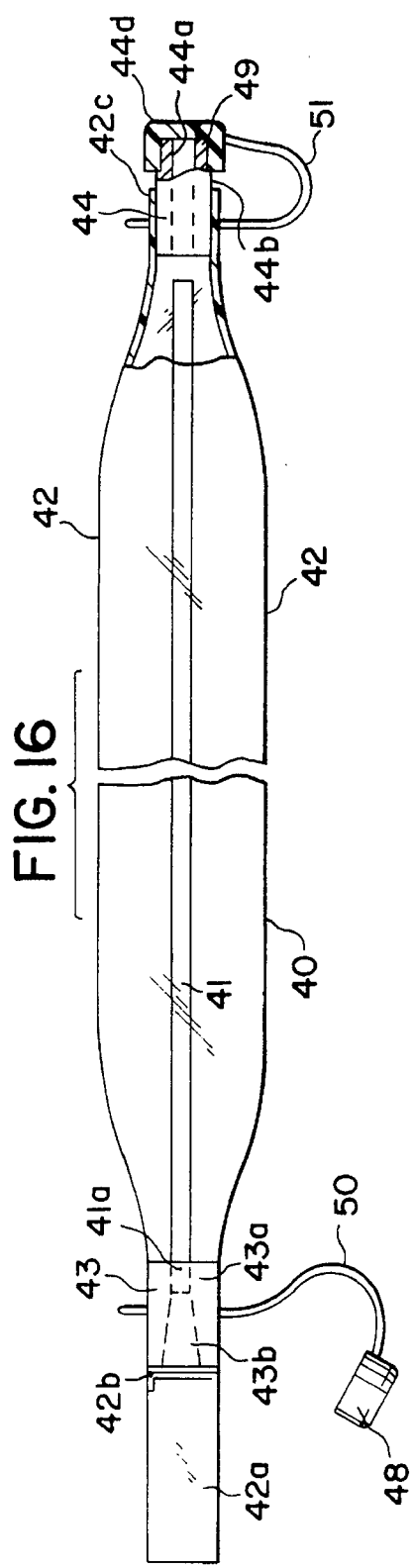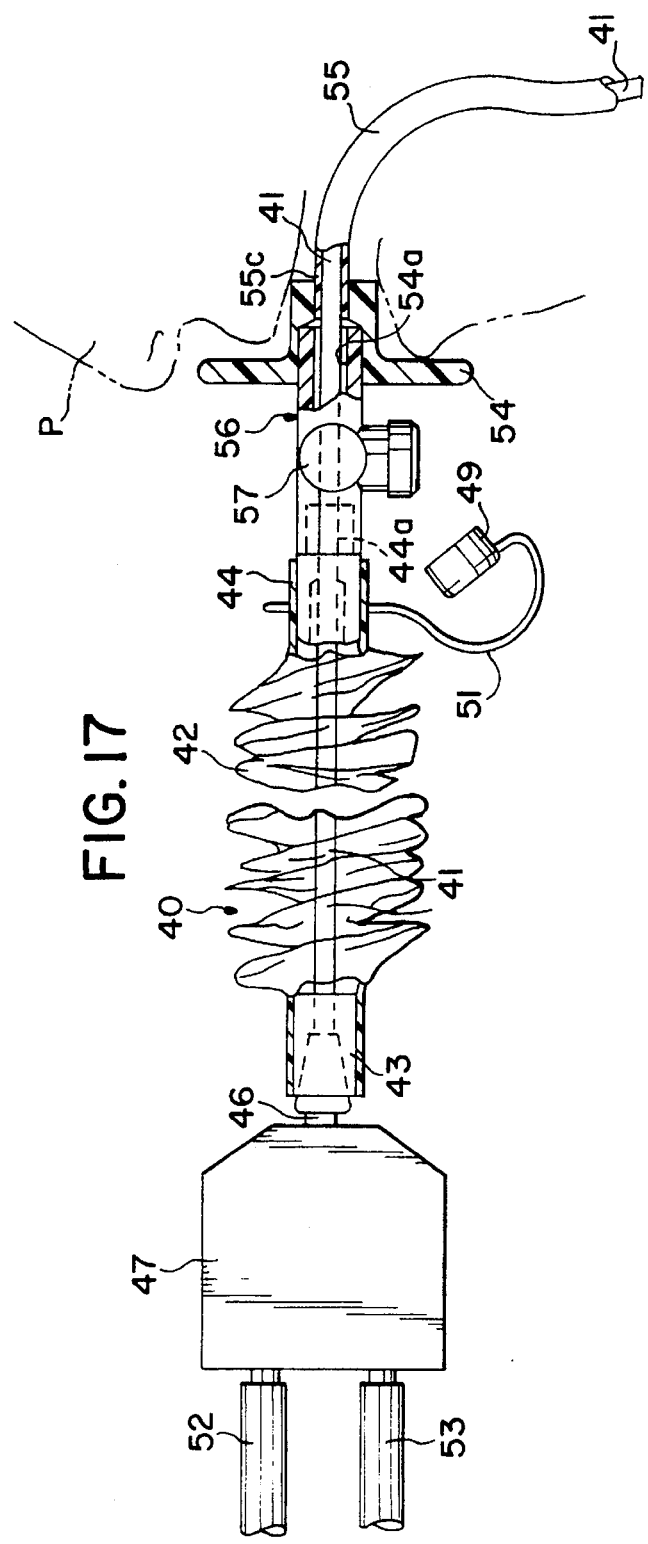

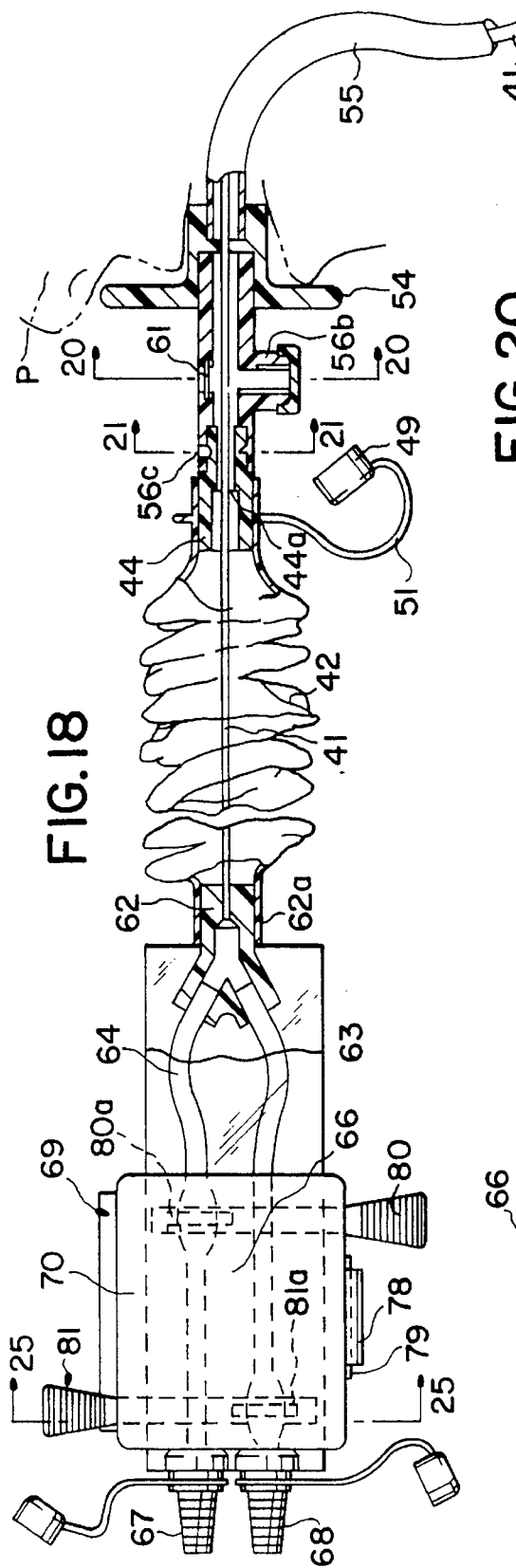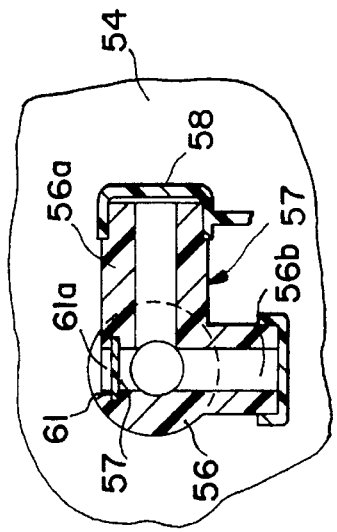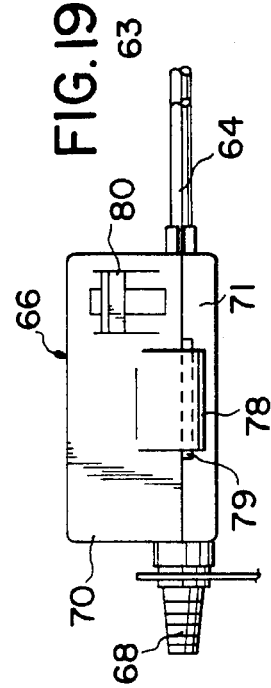

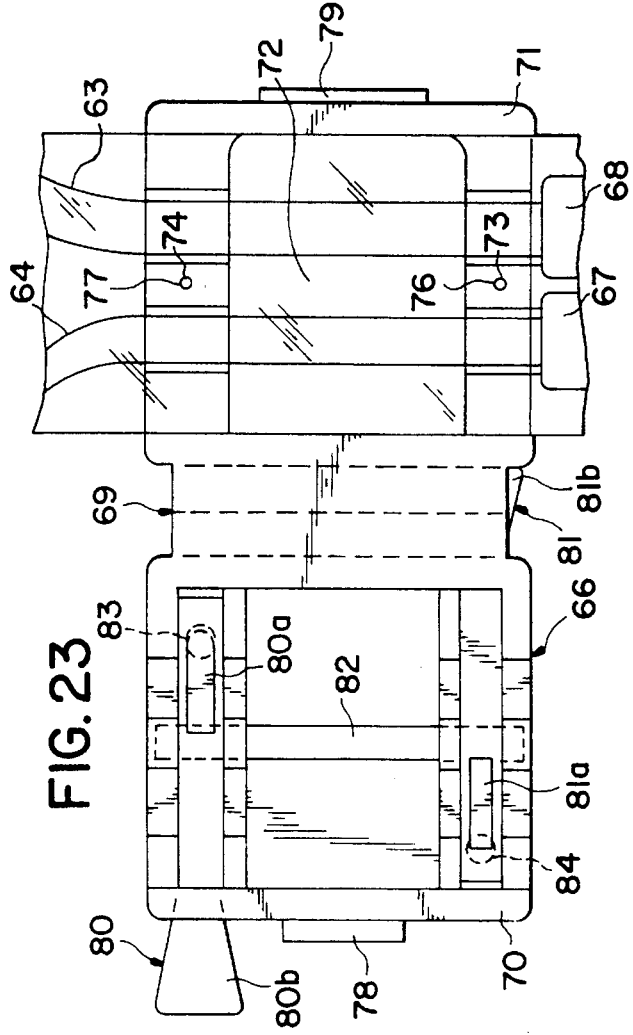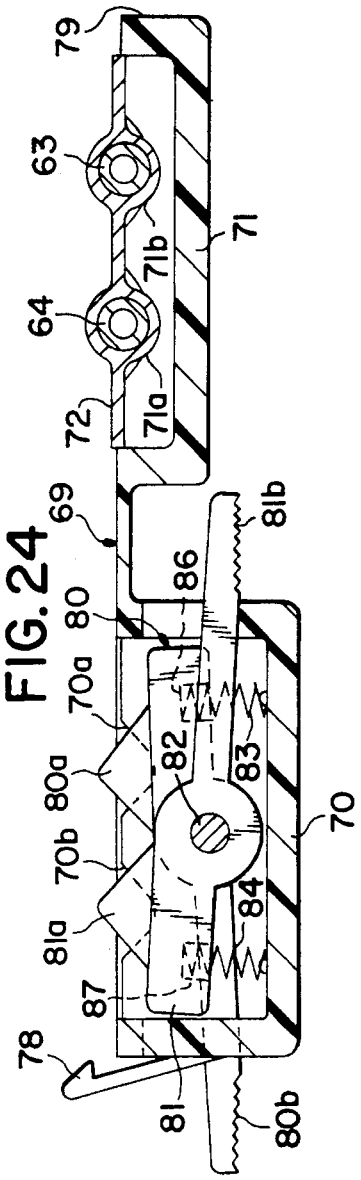

PRE-ASSEMBLED SEALED, SHEATHED CATHETERS AND RELATED VALVE ELEMENTS WITH QUICK DISCONNECT MEANS FOR ENDOTRACHEAL SUCTIONING

PRIOR APPLICATIONS

This application is a continuation-in-part of Ser. No. 07/520,787, filed May 8, 1990, which in turn is a continuation-in-part of application Ser. No. 07/520,787, filed Feb. 28, 1988, both abandoned.

BACKGROUND OF THE INVENTION

The present invention involves in part, a plastic envelope which converts into a sheath for catheters which are used for oxygenation and/or suctioning, particularly for such catheters adapted and intended to be attachable to and detachable from fluid suctioning and/or oxygenation sources. Sheaths of various kinds have been devised for such catheters to protect medical personnel from contact with body fluids and thereby expose such personnel to potential infection unless gloves and other protective clothing are worn. U.S. Pat. No. 4,569,344 discloses the use of a protective sheath for a respiratory device for this purpose. Simple suctioning catheters which include an opening for a therapist's thumb to control suctioning now provide sheaths extending from such opening to the distal end of the catheter but not otherwise. Protective catheter sheaths are also known and used for catheters other than oxygenation/suctioning as illustrated in U.S. patent Nos.: 3,861,395, 4,062,363, 3,709,223 and 3,937,220.

The present invention finds its utility in closed catheter systems for endotracheal insufflation and suctioning of comatose patients. Such patients are kept alive by respirators and accumulate fluid in tracheal areas which must periodically be removed in order to sustain life. In recent years, procedures have been initiated wherein endotracheal catheters used to remove such fluids are sealed within an outer flexible sheath to permit the therapist to place the catheter in the tracheal area and to withdraw the catheter therefrom for lavage cleansing (a process which is repeated several times) without exposing the therapist to contamination. The present state of the art puts such a system in place for a twenty-four hour period during which the same suctioning valve and sheathed catheter are used perhaps ten or more times. Examples of such sheathed catheter apparatus may be found in U.S. Pat. No. 4,569,344. It is an important objective of the concepts disclosed herein to permit easy and inexpensive replacement of contaminated parts used in an endotracheal suctioning procedure to minimize risk to the patient and to hospital personnel.

SUMMARY OF THE INVENTION

The protective catheter sheath of the present invention has several features not found or suggested by the above patents or in prior practice, features which lend themselves cooperatively to catheters which are meant to be attachable and detachable to and from oxygenation and/or suctioning sources and to tracheal devices placed in the patient to be treated. One aspect of this invention is to provide an inexpensive sterile package which converts to a sheath for individual catheters of this type. The invention provides means to convert the package to a protective sheath prior to oxygenation and/or suctioning of a patient and for reconversion of the sheath into a package to contain the catheter for disposal after it has been used. Thus medical personnel are at all times protected from infectious contamination during use of the catheter and after removal of the catheter from a patient.

More specifically with respect to a catheter and fluid sources of the type described, means are provided for connection between the proximate end of the catheter and a fluid source. A sealed elongated envelope of flexible plastic such as polyethylene initially packages and encapsulates the catheter. The package within the meaning and scope of the invention is any elongated plastic envelope which is sealed to contain a single catheter and thus preserve the sterility of the catheter before it is used.

In one of the embodiments disclosed, the fluid source has a catheter connecting means and the proximate end of the catheter includes connecting means for mating with the fluid source connecting means, one of the connecting means comprising a member defining a recess and the other of said connecting means comprising a projecting member. During such connection, the flexible sheet comprising the Catheter encapsulating envelope will be first stretched tautly across the catheter's connection member. The flexible sheet initially distends between the mating connecting means forming a seal therebetween. When the catheter connecting end is female, further movement of said connecting members to become fully mated causes the flexible sheet to rupture permitting a fluid passage to be established between the fluid source and the catheter. In another embodiment a similar connection is disclosed in which the Catheter comprises the male portion of the connector.

The catheter may obtain direct entry through the mouth or nose to the tracheal areas of the patient and essentially the same type of package/sheath attachment can be made to form a closed system by connection between the end of the distal end of the sheath catheter and an opening in a tracheal tube. The envelope thereafter forms a protective sheath about the catheter through which the catheter can be manipulated to be inserted and withdrawn from the tracheal areas of a patient.

After the catheter has been used during an endotracheal procedure, the plastic sheath reconverts into a package to contain the contaminated catheter. For this purpose the envelope has a tear-off extension which is initially separated to permit egress-of the distal end of the catheter and is thereafter retained. After the endotracheal procedure, the proximate end of the catheter is detached from the fluid source and both the proximate and distal ends of the catheter are brought together, the tear-off extension being used as a cap to cover both proximate and distal ends of the envelope to prevent any possibility that fluid may emerge to contaminate.

Another embodiment disclosed herein does not require the conversion of a package into a sheath but rather provides a novel pre-assembled and sealed sheathed catheter having quick connect and disconnect means for the proximate and distal ends thereof. According to this concept, a single oxygenation and suctioning valve may be used over a twenty-four hour period and at periodic intervals of, for example, two hours, an endotracheal procedure may be performed using a fresh sheathed catheter. This represents a considerable safety improvement to both patient and hospital personnel over current methods which use the same valve and sheathed catheter for multiple procedures for a twenty-four hour period. Furthermore, in accordance with this new invention, the construction of the sheathed easily replaceable catheter is so inexpensive that the cost per procedure is considerably lower than the cost per procedure of current equipment.

Finally, included herein is a concept which provides the ultimate protection to both patient and therapist. The concept involves a valve which uses resilient tubing for providing and controlling flow to the quick disconnect sheathed replaceable catheter, as heretofore described. In accordance with the new and advanced concept, the valve body opens to receive such tubing and closes to permit actuation of the valve by alternately crimping the tubing to shut off flow (preferably one tube for oxygen and another for suction flow) and by releasing the tubing to permit flow. The tubing at one end thereof is connected by quick disconnect means to a source of oxygen and a source of suction at the other end thereof to the endotracheal catheter. When a suctioning procedure has been completed, the entire assembly of valve tubing and sheathed catheters are quickly disconnected, disposed of and replaced by an identical uncontaminated assembly. The valve body may safely be used for multiple procedures since the only contaminated parts, i.e., the tubing and sheathed catheter are replaced after each procedure.

These and other aspects shall be further understood by examination of the following specification.

BRIEF DESCRIPTION OF THE DRAWING

FIG. 1 is a plan view of an endotracheal catheter encapsulated within a flexible plastic envelope which acts as a package for the catheter and subsequently as a sheath during use. The Figure further illustrates the inclusion/of a tear-off extension of the sheath/package envelope section for subsequent repackaging after use of the catheter;

FIG. 2 illustrates the catheter during an endotracheal procedure with the envelope serving as a protective sheath;

FIGS. 3–6 illustrate the attachment of the proximate end of the catheter and its female connecting means to a fluid source and the sequence of attachment wherein the envelope is anchored by the catheter connection to the fluid source, while a seal is formed between the mating parts;

FIGS. 7 and 8 illustrate the reconversion of the envelope into a package for the catheter;

FIG. 9 illustrates and discloses a novel adaptor/connector which may be used for the male attachment of a catheter and its sheath to a fluid source;

FIGS. 10 and 11 illustrate the sequential method of attachment of a catheter and its package/sheath to a fluid source in which the adaptor of FIG. 9 is employed;

FIGS. 16 and 17 illustrate an alternate embodiment comprising a preassembled, sealed, sheathed catheter with quick connect and disconnect means;

FIG. 18 is a plan view of a valve having replaceable valve elements (i.e. tubing) which are connected to a preassembled sheathed catheter with quick connect/disconnect means all of which are disposable and replaceable after each endotracheal procedure;

FIG. 19 is a side view of the valve shown in FIG. 18;

FIG. 20 is a section taken in the direction of arrows 20—20 of FIG. 18;

FIG. 21 is a section taken in the direction of arrows 21—21 of FIG. 18;

FIG. 22 is a detailed drawing of an improved "Bodi" type connecting member which interconnects the distal end of the disclosed endotracheal sheathed catheter assembly and the person requiring suctioning, including pressure relief and lavage means therein;

FIG. 23 is an enlarged plan view of the valve body of FIG. 18 illustrating the valve body opened to receive uncontaminated tubing elements or to permit removal and disposal of contaminated tubing elements;

FIG. 24 is a side view of the valve body of FIG. 23; and

FIG. 25 is a view of the valve body of FIGS. 23 and 24 shown in its closed (operative) condition, taken in the direction of arrows 25—25 of FIG. 18.

DESCRIPTION OF PARTICULAR EMBODIMENTS

Figure 12:
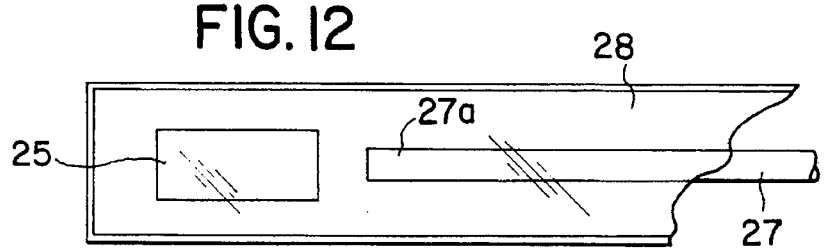
FIG. 12 illustrates the package/sheath encapsulation of the distal end of a catheter and a connector for making a closed (sheathed) connection between the distal end of the catheter and a tracheal tube which has been placed within the oral and tracheal cavities of a patient.

Referring to the drawing and initially to FIG. 1, a catheter 10 of a type which may be used for endotracheal procedures is contained and packaged within a flat elongated rectangular envelope 11. Envelope 11 is constructed of clear, flexible heat and/or pressure sealable plastic sheet material such as polyethylene having a thickness of 0.25 to 1 mil. Envelope 11 has a main section 12 which is somewhat longer than catheter 10 and is heat or pressure sealed along top and bottom edges 12a and 12b and ends 12c and 12d. Envelope 11 further includes section 13 which is likewise heat or pressure sealed along top and bottom edges 13a and 13b and along ends 13c and 12d. The seam at 12d is constructed so that section 13 may be readily torn off to free the distal end 10a of catheter 10. Catheter 10 is packaged and maintained within section 12 in a sterilized environment until section 13 is separated and section 12 is opened immediately prior to use of the catheter. Sections 12 and 13 shall be used subsequently in repackaging the catheter after its use, as will be described.

FIG. 2 illustrates the use of catheter 10 during one form of endotracheal procedure. The proximate end 10b of catheter 10 is adapted (as will be more fully explained) to be connected to a valve 15 which is connected to a source of oxygen 17 and suction 18. It will be understood that the distal end of catheter 10 has been exposed and placed within the tracheal/lung area of a patient P. Section 12, now acting as a sheath covers that portion of catheter 10 which shall be manipulated by the therapist. During the endotracheal procedure the patient's lungs may first be oxygenated, that is may be flooded with oxygen and subsequent thereto, fluid shall be suctioned from lung and bronchial areas. The procedure normally includes several repetitions of alternate oxygenation and suctioning with occasional withdrawal and insertion of catheter 10i to clear the catheter as it becomes blocked during suctioning. Section 12 as a sheath therefore protects the therapist during withdrawal of the catheter from the patient and its reinsertion from contact with bodily fluids which have contaminated the exterior of catheter 10. The sheath furthermore eliminates the need to wear protective gloves which themselves become externally contaminated if contact is made with a contaminated catheter. Gloves are usually of heavier weight material than section 12 to minimize tearing when the hand is inserted therein. This can make manipulation of a catheter difficult in contrast to a catheter contained within a sheath.

The connection between fitting 16 and adaptor 14 is of the "quick disconnect" type to allow multiple procedure endotracheal reuse of valve 13 for the same patient. A new sterile catheter will be used for each procedure and in a twenty-four hour period a dozen procedures may be required. The use of polyethylene as the material of section/sheath 12 provides a low friction surface between adaptor 14 and fitting 16 which eliminates potential sticking or binding between these parts to facilitate their quick disconnection.

A first illustrated conversion of section 12 from package to sheath for the aforesaid purpose will now be described.

Referring to FIGS. 3–6 in a form of connection where the proximate catheter connector is female, it will be seen that the proximate end 10b of catheter 10 has been fitted within a cylindrical member 14, which shall be referred to herein as an adaptor. Adaptor 14 in the illustrated embodiment, has a cylindrical bore 14a whose diameter is sized to fit the outside diameter of catheter 10 whose proximate end it receives and is cemented thereto. Bore 14a of adaptor 14 may be sized to accommodate various sizes of catheters. The other end of adaptor 14 has a cylindrical bore or recess 14b sized to mate snugly over a fitting 16 which projects from valve 15. Fitting 16 in the particular embodiment is of conventional design, is of molded plastic, having two generally frusto-conical segments 19 separated by grooves 20. Segments 19 each have a major diameter 19a which typically slightly exceeds the internal diameter of cylindrical recess 14b and segments 19 are rounded, at 19b to reduce friction as fitting 16 is forced progressively into cylindrical recess 14 to provide a snug fit. Adaptor 14 is preferably extrusion molded of a plastic material capable of sufficient deformation to accommodate the entry of fitting 16 within recess 14b. Despite the snug fit between segments 19 of fitting 16 and the exterior of adaptor 14 which may provide a fluid seal, it is possible for leakage to occur if either of segments 19 or recess 14b are out of round or pitted. As will be seen one of the aspects of the invention is to provide a supplementary sealing means to obviate such possible leakage.

The sequence of attaching catheter 10 to fitting 16 is illustrated in FIGS. 3–5. First, as illustrated in FIG. 3, the therapist will cause the end 12c of section 12 (avoiding the end seam) to be drawn tightly against the open end 14a of adaptor 14. Holding these elements in position between thumb and forefinger as shown, the adaptor 14 is then forced over fitting 16. As indicated in FIG. 4, initial insertion of fitting 16 into the cylindrical recess 14b of adaptor 14 will cause the end 12c of section 12 to be drawn within the adaptor recess and to be trapped between forward segment 19 of fitting 16 and the cylindrical wall 14b. Final movement of fitting 16 into adaptor 14 (FIG. 5) will rupture the end of 12c of section 12 prior to the seating of the adaptor against valve 13. Referring to FIG. 6, it will be observed that during the foregoing sequence, the membranous end 12c of section 12 becomes attenuated and wedged between the forward segment 19 of fitting 16 and the bore 14b. This anchors the end 12c of sheath 12 while permitting fluid flow to occur between catheter 10 and valve 15. Furthermore the end 12c of section 12 forms a seal between the adaptor and the valve 13 at 21; and forms an O-ring like seal 22 between the interior of cylindrical wall 14b and segment 19 which prevents leakage between the valve 13 and adaptor 14.

Referring to FIGS. 9–11 a similar connection of a catheter with a fluid source will be seen where the catheter connection is male and the fluid source connection is female The same concept shall apply where the proximate end of the catheter is inserted directly into an orifice communicating with a fluid source. However, the following disclosure also illustrates the use of a variable diameter connector 20, one end 20a of which fits over a nipple 21 connected to a fluid source while the other end 20b thereof receives the proximate end of a catheter 22. The connector 20 is of unique construction. It is conventionally formed of a resilient rubber-like material which permits the connected ends thereof to be distended, for example when slipped over the nipple 21 attached to the fluid source and when the catheter 22 is inserted into the opposite end. The connector 20 shall have an internal diameter which normally permits and accommodates the respective attachments to nipple and catheter with some gripping action therebetween because of the resilient nature of the material used to construct the adaptor. The present invention further provides, however that the connector shall be constructed to have essentially non-stretching fibers 20c (see FIG. 9) lining and embedded within the cylindrical wall of the connector whose principal function resulting from the crossing pattern of fibers has been illustrated is to cause the adaptor to be contracted in diameter if the adaptor is pulled or stretched in an axial direction. The principle is the same as that used in a Chinese finger trap but has particular applicability should the proximate end of the catheter 22 be pulled or jerked by the therapist or patient and begin to slip out of its internal mating connection within the adaptor 20. The adaptor 20, as constructed, thereby provides additional gripping for this purpose beyond the inherent resilience of the adaptor.

FIGS. 10 and 11 disclose the method of making the connection between the proximate end of the catheter and the adaptor 20 to attach the catheter package/sheath. In this embodiment, the therapist will secure the end of the polyethylene package 23 tautly over the proximate end 22a of the catheter as shown in FIG. 10 and then use a sterile device 24 to puncture the polyethylene film 23a drawn across the end of the catheter. Thereafter the catheter 22 may be inserted within the end 20b of the adaptor 2) which requires distention of the diameter of the adaptor in order to effect such entry. The interior of the adaptor should be roughened to assist frictional engagement between the outside diameter of the catheter and its sheath. To assist in the frictional engagement between the respective surfaces it may be desirable to provide the interior and exterior surfaces of the sheath and the exterior surface of the catheter with a roughened or pebbled surface. During forced entry of the catheter within the adaptor end 20b the pierced or ruptured end of the package will be drawn away from the opening 22a in the catheterland a seal will be formed between the catheter and adaptor by the sheath 23 which interfaces between both these surfaces.

Figure 13:
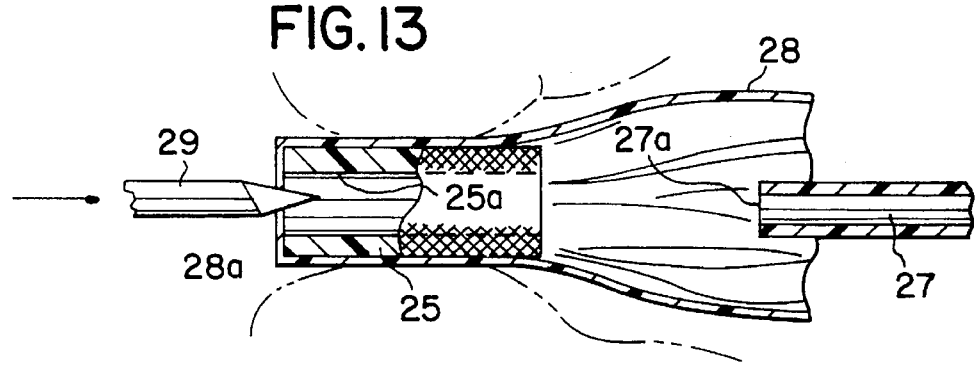
FIGS. 13 and 14 illustrate the sequential connection of the distal end of the package/sheath and the connector therein within an orifice provided in a tracheal tube extending into the tracheal and oral cavities of a patient. The Figure further illustrates the admission of the distal end of the catheter through the connector and into the aforesaid tracheal cavity while maintaining a (closed sheath) connection between the package/sheath and the tracheal tube.
Figure 14:
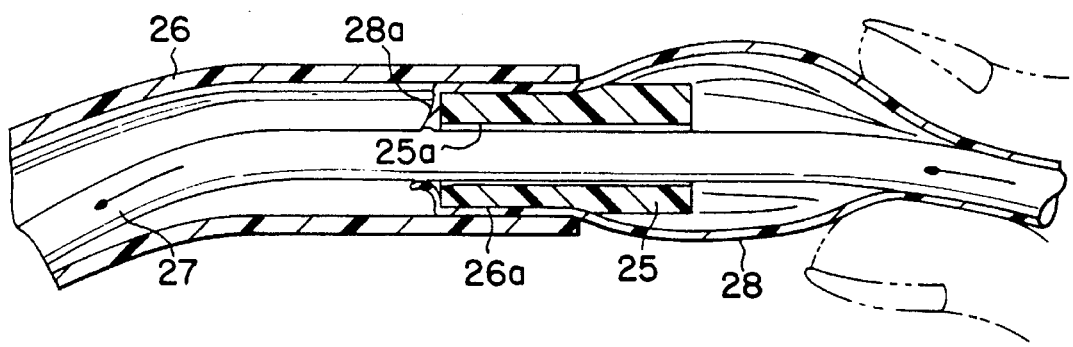

Referring to FIGS. 12–14 it will be seen that the present invention permits the package/sheath containing a suction catheter, for example, to be used to form a "closed system" between the patient and a fluid source. A closed system may be defined as the catheter connections between a fluid source and a patient which are sheathed both proximally and distally. Male and female sheathed connections to a fluid source have thus far been described. A sheathed or closed connection between the catheter and the patient shall now be described. It will be observed (FIGS. 11 and 12) that within the package containing the catheter a cylindrical connector 25 preferably of plastic material has been included. The connector 25 has an outer diameter which is sized to fit snugly within an opening 26a formed in a tracheal tube 26 located within the oral cavity and the throat of a typically comatose patient. Such patients are required to be placed on a respirator and the opening 26a may be used for this purpose. In the present illustration opening 26a in the tracheal tube 26 shall be illustrated as a means for providing entry of a suction catheter 27 into the tracheal area of the patient. For purposes of simplicity of illustration a single opening in the tracheal tube has been illustrated; however, it will be understood that dual openings may be provided one of which may be used to provide continuous respiration of the patient while a suctioning procedure is taking place through the alternate opening.

FIGS. 13 and 14 illustrate the manner in which the distal end of the package/sheath 28 may be connected to the tracheal tube 26 to provide a closed system. Accordingly, connector 25 will be held by the therapist tautly against the end of the package after section 13a has been removed therefrom. Connector 25 has been provided with a circular passage 25a slightly larger in diameter than the outside diameter of catheter 27. The therapist will puncture the package/sheath end 28a with a sharp sterile instrument 29 to provide an opening therein immediately adjacent to the passage 25a. When the connector 25 is inserted within the opening 26a in the tracheal tube 26, the connector 25 will secure the end of the package/sheath 28 in a manner similar to that previously described. Thereafter the therapist by manipulating the distal end 27a of the catheter may cause the distal end 27a to pass through passage 25a in the connector and into the tracheal regions of the patient to effect a suction procedure, while a closed system (sheath enclosed) has been effected between the fluid source and the patient.

Figure 15:
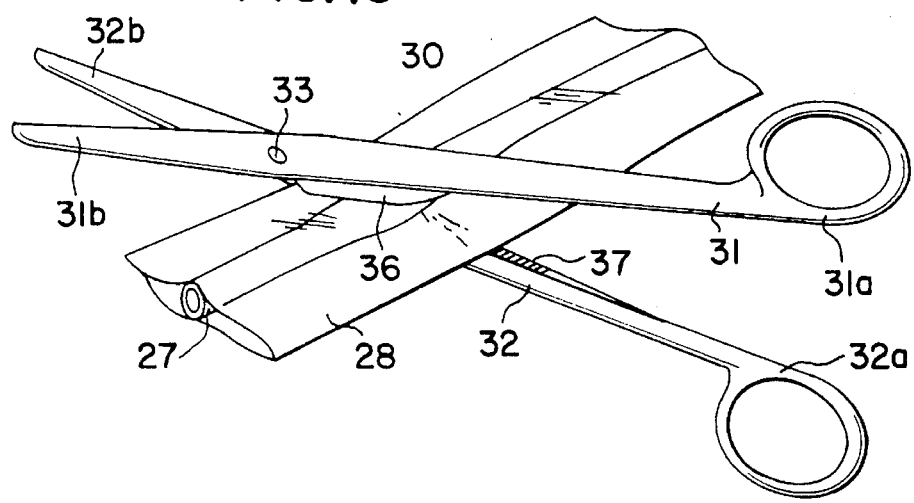
FIG. 15 illustrates the use of clamping means for pinching closed or permitting to open a catheter which has been sheathed by means of the package/sheath concept of the invention.

FIG. 15 illustrates a method for controlling suction flow through catheter 27 once a closed system has been established as described. For this purpose the modified scissors device 30 may be used. Legs 31, and 32 thereof are hinged at 33 to form section 31a, 31b and 32a, 32b. Thumb and forefinger openings 34 and 35 are provided in sections 31a and 32a for the therapist. Section 31a has an elongated projection 36 extending toward the mating flat section 37 of section 32a so that when sections 31a and 32a are located as illustrated about sheath 28 and catheter 27 contained therein, movement by the therapist of sections 31a, 32a toward each other will cause catheter 27 to be crimped shut as shown. Release of pressure on the catheter will permit fluid flow, for example suction, to continue. This method is far superior to the use of the "thumb sucker" which requires the therapist to control suction by means of an opening in the catheter since the present method permits the catheter to be entirely sheathed.

Referring to FIGS. 7 and 8, the reconversion of envelope 12 to a disposal package for catheter 10 has been illustrated. After an oxygenation and/or suctioning procedure has been completed, the therapist will remove the distal end 10a of catheter 10 from the patient and extend the sheath section 12 and end 12d thereof beyond the distal end 10a of the catheter. This may be done with a gloved hand and with the use of scissors 30, sections 31b and 32b being designed for this purpose. Sheath end 12d may then be folded over and secured to cover the distal end of the catheter by attaching thereto a strip of pressure sensitive adhesive tape 17. The use of such tape should avoid direct contact with end 12d of section 12 which may have been contaminated. The therapist may then detach the catheter from valve 13 and fold over the end 12c securing same by tape 18.

At this time the open ends of sheath section ends 12c and 12d may be sealed with tape and section 12 may be disposed of, but it is preferred that the following steps be taken. Accordingly, the therapist shall bend sheath 12 including catheter 10 upon itself until ends 12c and 12d of section 12 are adjacent. Section 13 may then be slipped over ends 12c and 12d as a cap and when sealed by tape 23, the contaminated catheter is safely secured for disposal.

The preassembled, sheathed endotracheal catheter assembly 40 illustrated in FIGS. 16 and 17 shall now be described. The catheter assembly consists primarily of an endotracheal catheter 41 which is encapsulated by a fluid tight sheath 42 attached by being bonded, preferably by being shrunk fit around the cylindrical outer surfaces of connectors 43 and 44. The proximate end 41a of catheter 41 is received and cemented within a cylindrical recess 43a provided in connector 43, a truncated conical recess 43b being also provided to secure quick connect/disconnect fitting 46 projecting from insufflation (oxygenation) suctioning valve 47. Sheath 42 may be provided with a tear-off extension 42a which is serrated at 42b perpendicular to the axis of recess 43b. Although not illustrated, a similar tear-off strip may be provided at the distal end 42c of sheath 42, the present illustration showing the sheathed catheter as it would appear after removal of the tear-off Strip located adjacent to connector 44. The purpose of tear-off strips at each end of sheath 42 is to preserve sterility of the interior of the sealed (sheathed) catheter 41, the interior of the sheath and of the openings in connectors 43 and 44 prior to removal thereof. Distal connector 44 has a cylindrical bore 44a to permit egress of the catheter from the sheath 42 as will be described.

Completing the description of FIG. 16, caps 48 and 49 have been provided which are attached by tethers 50, 51 to connectors 43 and 44. Cap 49 has been shown in place over the end of connector 44 and in this position cap 49 may also be used to function as sealing means in the same manner as does tear strip 42a, however, such tear strips are thought to be a more reliable means of preserving internal sterility. Caps 48 and 49 are particularly useful as a means for preventing the egress of contaminant fluid from the interiors of catheter 41 and sheath 42 after an endotracheal procedure has been completed, and the contaminated catheter and its sheath have been disconnected for disposal.

Referring to FIG. 17 it will be observed that connectors 43 with sheath 42 sealed thereto in fluid tight relation is simply and quickly connected to valve 47 by connector 46. Oxygen flows into valve 47 by way of tube 52 while suction is provided through tube 53. On the distal end of the sheathed catheter assembly a patient requiring treatment has been shown having a mouthpiece 54 connected to intubation tube 55 which will guide catheter 41 into the tracheal areas of the patient. Since most patients who require endotracheal suctioning are comatose they are "intubated" to facilitate this procedure which also facilitates connecting the patient to a respirator (not shown). An intermediate connector known as a "Bodi" connector is routinely inserted into the mouthpiece opening, and the patient will be connected to a respirator through the Bodi connector. An improved Bodi connector has been indicated in the drawing by reference numeral 56 and has been illustrated in FIGS. 17, 20 and 22. The connector 56 has a cylindrical passageway 56a which provides a straight connection between the bore 44a of connector 44 and the bore 55a of intubation tube 55. As shown in FIGS. 20 and 22 connector 56 has a cylindrical extension 57 perpendicular to bore 55a which is adapted to be connected to a respirator (not shown). Extension 57 is provided with a cap 58 to be applied when a patient is removed from the respirator.

As seen in FIGS. 17 and 22 connector 44 has two outer diameters 44b and 44d. Diameter 44b is dimensioned to have an outer diameter which is the same as, or somewhat larger than, the outside diameter of connector 56. This has been done to prevent bonded end of sheath 42 (which may not be entirely smooth after being shrunk-fit to connector 44) from interfering with the fluid tight connection between connectors 44 and 56. To assure that such connection is secure, the interior of connector 56 has been provided with pin 56c which is received within spiral groove 44e so that rotation of connector 44 as it is inserted into the cylindrical passageway 56a shall produce a fluid tight bayonet type connection.

Connector 56 has been equipped with pressure relief/lavage means which consists of a circular rubber diaphragm 61 having a slit 61a therein. Immediately below the diaphragm is a thin filter 57 constructed of tough non-frangible material such as nylon whose purpose shall be explained. During insufflation of a patient, it is important that pressure in the tracheal areas not be permitted to exceed a pressure greater than for example four pounds above atmospheric pressure. The slit 61a in diaphragm 61 will be set to relieve such excessive pressure. The purpose of filter 57 is to allow such pressure to be relieved while preventing external aspiration of fluid.

Normal endotracheal suctioning procedure requires the catheter 41 to be inserted fully and then slowly withdrawn. Suction is maintained continuously during withdrawal in order to remove fluid more completely. Mucous will be scraped from the exterior of catheter 41 as the catheter is withdrawn into bore 44a of connector 44 and will be collected within Bodi connector section 56a immediately below diaphragm 61. After completion of a procedure, a saline solution shall be injected from a needle syringe through slit 61a to lavage the interior of the body connector. Cap 56b shall be removed from section 56a to permit flushing from this section into a waste receptacle. The construction of diaphragm 61 shall permit passage of the needle from a syringe without impairing its pressure relief function. It should be noted that the central placement and location of diaphragm 61 and of slit opening 61a therein cooperate to permit considerable rotary movement of the syringe needle internally of the Bodi connector to spray a saline solution throughout the interior of connector 56.

It will be understood that because the illustrated parts are preassembled, sealed and maintained in sterility until immediately prior to use, the patient is protected from external contamination, and during an endotracheal procedure the therapist is also protected from contamination from the patient. Immediately upon completion of a procedure, the catheter is withdrawn into its sheath, and the distal end of the assembly may be quickly disconnected, tipped upwardly and capped to prevent leakage of contaminant fluid trapped within the catheter 41 and sheath 42. Similarly disconnection and capping may be made at the proximate (valve) end of the assembly followed by disposal.

The simplicity of the replaceable catheter/sheath assembly according to the present invention makes it possible over a twenty-four hour period (a) multi-use of an oxygenation,i suctioning valve, (b) multi-replacement of such preassembled sheathed, sterile catheters at very little expense and; (c) maximum protection to the patient and the administering therapist.

In a final embodiment of this invention illustrated in FIGS. 18, 19 and 23–25, complete quick connect/disconnect replaceability of all fluid conducting parts contaminated during a single endotracheal procedure is made possible. For simplicity where the elements and parts already described are the same, the same reference numerals used in describing FIGS. 16 and 17 have been used. Accordingly the concept retains the described constructions relating to the sheathed catheter 41, its sheath 42, the distal connection with body connector 56 and the patient and so on. However, proximate connector 43 is not directly connected to a valve but has been replaced by Y-connector 62 whose outer cylindrical surface 62a is bonded, preferably by shrink-fitting around its outer cylindrical surface the proximate end of sheath 42. Connector 62 also secures resilient tubing members 63 and 64 which extend through valve body 66 and are respectively joined to external connectors 67 and 68 to receive oxygen and to receive suction. The valve body 66 provides means which shall be described to alternately crimp closed and release each tubing member 63 and 64 in order to provide alternately oxygen or suction to catheter 41.

Referring to FIGS. 23 and 24, it will be seen that valve body 66, which has been constructed of injection molded plastic has been provided with a hinge 69 which permits the valve body to be opened to completely expose the mating and adjacent interior surfaces of the valve sections 70 and 71. Each of these sections has semi-circular mating grooves 70a, 70b and 71a, 71b which define means for receiving tubing members 63 and 64 when the valve body has been opened into the position of FIG. 24. While not essentiel to the basic concepts of replaceability, the tubing members 63 and 64 may be encapsulated in thin resilient plastic sheets which collectively have been designated as reference numeral 72. Such plastic encapsulation shall position tubing members 63, 64 precisely relative to each other for lateral insertion in grooves 71a, 71b (FIG. 24). Locating holes 73 and 74 in plastic sheets 72 have also been provided to receive locating pins 76, 77 in valve part 71 to assist precise longitudinal location of tubing members, and connectors 67 and 68. Another advantage attendant with the aforesaid plastic encapsulation is the secondary sealing effect achieved with respect to the joinder of tubing members 63, 64 to connectors 67, 68 and to Y-connector 62.

FIG. 25 illustrates the valve body 66 in its closed, operative position held securely in such position by latch member 78 connected to valve body part 70, which may be snapped over tang 79 integrally formed with valve part 71. In order to control flow in tubing members 63, 64, actuating levers 80 and 81 have been provided which are hinged along a common axis generally at their centers about hinge pin 82 located in valve body section 70. Hinge pin 82 is located centrally above and intermediate tubing members 63 and 64. Each actuator has been constructed to have at one, end thereof a depending crimping extension 80a and 81a, and at their opposite ends a section 80b and 81b which may be depressed to raise each crimping extension out of crimping contact with a respecting tubing member 63 and 64. Springs 83, 84 are mounted in cylindrical recesses 86, 87 in valve section 70 as shown in order to cause crimping extensions to close each of tubing members 63, 64 against fluid flow therein where an actuator 80 or 81 is not depressed, which is the position illustrated in FIG. 25. This assures that all fluid flow shall cease when the therapist ceases to depress either of the actuators. The actuators must be depressed individually at opposite sides of the valve to permit oxygen to flow or to provide suction.

Theoretically, valve body 66 would accommodate replaceability of all valve tubing, connecting members, the endotrachel catheter and its sheath after each endotracheal procedure for an unlimited period of time. Certainly, such replaceability would maximize protection of the patient and hospital personnel over a twenty-four or forty-eight hour period without replacement of the valve body. Replacement of all contaminated parts is simple and quickly achieved. Finally, the cost per procedure for replacement of contaminated components is minimal.

It will be understood that the foregoing description has been of particular embodiments. In order to understand the inventive scope disclosed herein, reference should be made to the appended claims.

We claim:

1. In combination with an endo-trachial suctioning system for removal of fluid during a suctioning procedure from the trachial region of a person requiring such removal, said system including a suction source, a valve connected to said suction source, an intubation tube extending from the oral cavity of said person requiring said suctioning procedure into said trachial region and an intubation tube connector means extending from said intubation tube and from said oral cavity; the invention comprising: a pre-assembled group of endo-trachial suction components for replaceable use within said endo-trachial system wherein said components are interconnected and arranged to form a self-contained package the interior of which is sealed to provide a sterile environment, said package having means to permit unsealing of said package and quick connect/disconnect insertion thereof into the aforesaid endo-trachial suctioning system between said valve and the intubation tube connector means; and wherein after completion of a said procedure and removal of said package of said components from said system, said package is adapted to be re-sealed to contain residual contaminants therein resulting from said endotrachial suctioning procedure: the arrangement, construction and interconnection of said endo-trachial suctioning system and said package comprising:

a) a suction catheter of sufficient length generally to extend from said valve through said intubation tube connector means and through said intubation tube into the trachial region of a person to be treated;

b) a flexible tubular sheath of sufficient length to contain said catheter and means for fully withdrawing said catheter into said sheath;

c) two cylindrical sheath connecting members each having an external diameter corresponding to the internal diameter of said sheath;

d) the first of said connecting members defining therethrough an axial bore of approximately the same diameter as the outside diameter of said catheter, and means permanently to affix therein one end of said catheter;

e) the second of said connecting members defining therethrough a bore of a diameter slightly larger than the outside diameter of said catheter to permit free passage of said catheter therethrough;

f) means for attaching in fluid-sealed relation said first and second connecting members to said sheath within opposite ends of said sheath with the bores of said first and second connecting members being in alignment; and with the ends of said bores facing outwardly of said sheath being exposed at opposite ends of said sheath;

g) sealing element means connected to each of said first and second connecting members for sealing, unsealing and resealing each of the exposed bores in said first and second connecting members;

h) quickly connectible/disconnectible means for establishing a sealed fluid connection between said valve and said first connecting member;

i) quickly connectible/disconnectible means for establishing a sealed connection between said intubation tube connector and said second connecting member;

whereby said first and second connecting members together with said catheter and said sheath a) are sealed and sterilized as a contaminant free package prior to use in an endo-trachial suctioning procedure;

b) are unsealed and quickly connected in sealed relation to a suction valve and to an intubation tube to permit an endo-trachial suctioning procedure to be performed;

c) and after completion of such procedure are resealed for disposal as a package containing contaminants resulting from such procedure.

* * * * *